(12) United States Patent
Wang et al.

(10) Patent No.: US 12,727,857 B2
(45) Date of Patent: Sep. 8, 2026

(54) PROBE HOLDER AND ULTRASOUND IMAGING SYSTEM

(71) Applicant: GE Precision Healthcare LLC, Waukesha, WI (US)

(72) Inventors: Xiaoren Wang, Wuxi (CN); Hua Ji, Wuxi (CN); Linbo Yang, Wuxi (CN); Lei Xia, Wuxi (CN); Dongsheng Xu, Wuxi (CN)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/886,903

(22) Filed: Sep. 16, 2024

(65) Prior Publication Data

US 2025/0090139 A1 Mar. 20, 2025

(30) Foreign Application Priority Data

Sep. 18, 2023 (CN) ........................ 202311206231.3

(51) Int. Cl.
*A61B 8/00* (2006.01)

(52) U.S. Cl.
CPC .................................. *A61B 8/4455* (2013.01)

(58) Field of Classification Search
CPC ... A61B 8/4455; A61B 8/4209; A61B 8/4281; A61B 8/4218; A61B 8/4227; G10K 11/004; G10K 11/352
See application file for complete search history.

(56) References Cited

U.S. PATENT DOCUMENTS 5,673,696 A * 10/1997 Bidwell ............... G10K 11/004 600/437
7,029,446 B2 4/2006 Wendelken
2006/0241476 A1* 10/2006 Loubser ............... A61B 8/4209 600/463
2018/0263438 A1* 9/2018 Verchick ............... A47K 13/26
2022/0240896 A1 8/2022 Meurer

FOREIGN PATENT DOCUMENTS

JP 6266356 B2 1/2018

* cited by examiner

*Primary Examiner* — Bo Joseph Peng

(57) ABSTRACT

A probe holder used for an ultrasound imaging system, comprising: an upper holding portion, the upper holding portion comprising a first cavity formed by a surrounding an inner surface, an upper end of the first cavity comprising an upper opening, the inner surface contracting inward at a lower end of the first cavity to form a lower opening, and the size of the lower opening being smaller than the size of the upper opening; a lower holding portion, the lower holding portion comprising a second cavity formed by the inner surface passing through the lower opening, the inner surface contracting inward at a lower end of the second cavity to form a bottom opening, and the size of the bottom opening being smaller than the size of the lower opening; and a side opening.

9 Claims, 5 Drawing Sheets

PROBE HOLDER AND ULTRASOUND IMAGING SYSTEM

CROSS-REFERENCE TO RELATED APPLICATION

This application claim priority to Chinese Patent Application No. 202311206231.3, which was file on Sep. 18, 2023 at the Chinese Patent Office. The entire contents of the above-listed application are incorporated by reference herein in their entirety.

TECHNICAL FIELD

The present invention relates to the field of medical imaging, and in particular, to a probe holder for holding a probe, and an ultrasound imaging system including the probe holder.

BACKGROUND

In ultrasound imaging technology, a probe is typically used to transmit an ultrasonic signal to a site to be scanned and receive an ultrasonic echo signal. Further, the echo signal is processed to obtain an ultrasound image of the site to be scanned. Different probes may be required for different sites to be scanned. Therefore, a plurality of different probes may be provided for the same ultrasound imaging system, and a user may select a suitable probe for ultrasound scanning according to actual requirements. A probe that does not need to be used may be held and fixed by means of a probe holder.

Different probes have different sizes and shapes. For example, a 4D probe is typically relatively large in size due to having a complex internal structure. Alternatively, an intracavitary probe typically has an elongated cylindrical structure to adapt to a natural cavity. To adapt to probes of different outer surface sizes, the probe holder also needs to be provided with different shapes. When placing the probe, the user needs to select a probe holder that matches the probe according to the type of the probe. This increases the burden on the user and increases time consumption, and also increases manufacturing costs of the probe holder.

SUMMARY

The aforementioned defects, deficiencies, and problems are solved herein, and these problems and solutions will be understood through reading and understanding the following description.

Some embodiments of the present application provide a probe holder used for an ultrasound imaging system, comprising: an upper holding portion, the upper holding portion comprising a first cavity formed by a surrounding an inner surface, an upper end of the first cavity comprising an upper opening, the inner surface contracting inward at a lower end of the first cavity to form a lower opening, and the size of the lower opening being smaller than the size of the upper opening; a lower holding portion, the lower holding portion comprising a second cavity formed by the inner surface passing through the lower opening and continuing to extend downward by a certain distance, the inner surface contracting inward at a lower end of the second cavity to form a bottom opening, and the size of the bottom opening being smaller than the size of the lower opening; and a side opening, the side opening penetrating outward through the probe holder from the inner surface, and extending from the upper opening to the bottom opening.

Optionally, the first cavity and the second cavity each have a continuous and smooth inner surface, the first cavity is configured to hold a probe of a first size, the second cavity is configured to hold a probe of a second size, and the second size is smaller than the first size.

Optionally, an inner surface of the first cavity comprises a circular arc structure that gradually contracts from the upper opening to the lower opening, and a part of the circular arc structure close to the lower opening has a reduced curvature.

Optionally, the size of a part of the inner surface of the first cavity close to the upper opening gradually increases to form a probe guide portion.

Optionally, an inner surface of the second cavity contracts inward along a straight line to form a cylindrical structure having a gradually decreasing inner diameter.

Optionally, the bottom opening comprises a stepped structure.

Optionally, the probe holder further comprises a cable recess, the cable recess being formed by the inner surface extending outward from the bottom opening to the upper opening, and the cable recess obliquely extending substantially along a straight line from the bottom opening to the upper opening.

Optionally, the width of the cable recess at the bottom opening end gradually decreases from outside to inside.

Optionally, an extension depth of the cable recess at the bottom opening end is greater than the diameter of the bottom opening.

Optionally, the probe holder further comprises an elastic body, the elastic body comprising the upper holding portion, the lower holding portion, and the side opening, the elastic body being detachably mounted in a body of the probe holder, and the size of an outer surface of the elastic body matching the size of an inner surface of the body of the probe holder.

Optionally, a top portion of the elastic body comprises a convex edge, a bottom portion of the elastic body comprises a plurality of protrusions, and the elastic body engages with the inner surface of the body of the probe holder by means of the convex edge and the plurality of protrusions.

Optionally, the probe holder further comprises a cable recess, the cable recess being formed by the inner surface extending outward from the bottom opening to the upper opening, and the shape of the cable recess enabling the elastic body to be mounted in the body of the probe holder only from a certain specific angle.

Optionally, the probe holder is provided at an edge of a control panel of the ultrasound imaging system.

Optionally, the probe holder is detachably connected to a main body of the ultrasound imaging system.

Further provided in some embodiments of the present application is an ultrasound imaging system, the ultrasound imaging system comprising any one of the probe holders described above.

Optionally, the probe holder comprises a plurality of probe holders provided at an edge of a control panel of the ultrasound imaging system, and the plurality of probe holders have shapes that are the same as or symmetrical to each other.

It should be understood that the brief description above is provided to introduce, in a simplified form, concepts that will be further described in the detailed description. The brief description above is not meant to identify key or essential features of the claimed subject matter. The scope is defined uniquely by the claims that follow the detailed description. Furthermore, the claimed subject matter is not limited to implementations that solve any deficiencies raised above or in any section of the present disclosure.

BRIEF DESCRIPTION OF THE DRAWINGS

The present application will be better understood by reading the following description of non-limiting embodiments with reference to the accompanying drawings, where.

DETAILED DESCRIPTION

Specific embodiments of the present invention will be described below. It should be noted that in the specific description of the embodiments, it is impossible to describe all features of the actual embodiments of the present invention in detail, for the sake of brief description. It should be understood that in the actual implementation process of any embodiment, just as in the process of any one engineering project or design project, a variety of specific decisions are often made to achieve specific goals of the developer and to meet system-related or business-related constraints, which may also vary from one embodiment to another. Furthermore, it should also be understood that although efforts made in such development processes may be complex and tedious, for a person of ordinary skill in the art related to the content disclosed in the present invention, some design, manufacture, or production changes made on the basis of the technical content disclosed in the present disclosure are only common technical means, and should not be construed as the content of the present disclosure being insufficient.

Unless otherwise defined, the technical or scientific terms used in the claims and the description should be as they are usually understood by those possessing ordinary skill in the technical field to which they belong. "First", "second", and similar words used in the present invention and the claims do not denote any order, quantity, or importance, but are merely intended to distinguish between different constituents. The terms "one" or "a/an" and similar terms do not express a limitation of quantity, but rather that at least one is present. The terms "include" or "comprise" and similar words indicate that an element or object preceding the terms "include" or "comprise" encompasses elements or objects and equivalent elements thereof listed after the terms "include" or "comprise", and do not exclude other elements or objects. The terms "connect" or "link" and similar words are not limited to physical or mechanical connections, and are not limited to direct or indirect connections.

Figure 1:
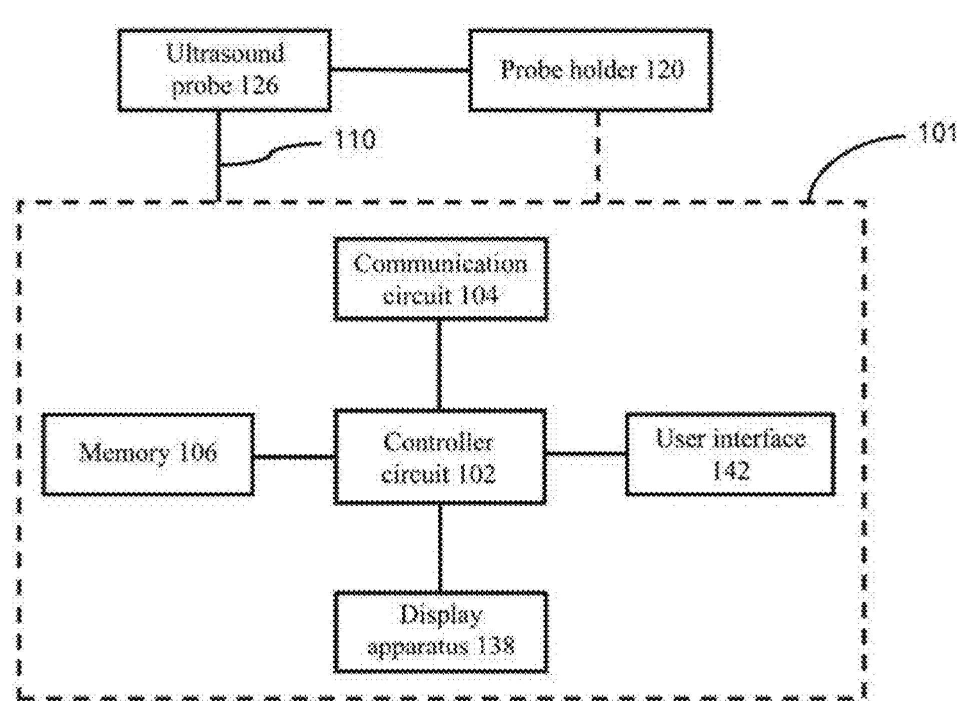
FIG. 1 is a schematic diagram of an ultrasound imaging system 100 according to some embodiments of the present application.

FIG. 1 is a schematic block diagram of an ultrasound imaging system 100. The ultrasound imaging system 100 may include a host 101, a probe holder 120, and a probe 126. The probe 126 is connected to the host 101 by means of a cable 110. Further, the host 101 may include a controller circuit 102, a display apparatus 138, a user interface 142 and a memory 106 that are connected to a communication circuit 104.

The controller circuit 102 is configured to control operation of the ultrasound imaging system 100. The controller circuit 102 may include one or more processors. Optionally, the controller circuit 102 may include a central processing unit (CPU), one or more microprocessors, a graphics processing unit (GPU), or any other electronic component capable of processing inputted data according to a specific logic instruction. Optionally, the controller circuit 102 may include and/or represent one or more hardware circuits or circuit systems, and the hardware circuit or circuit system includes, is connected to, or includes and is connected to one or more processors, controllers, and/or other hardware logic-based apparatuses. Additionally or alternatively, the controller circuit 102 may execute an instruction stored on a tangible and non-transitory computer-readable medium (e.g., the memory 106).

The controller circuit 102 is operatively connected to the display apparatus 138 and the user interface 142. The display apparatus 138 may include one or more liquid crystal display apparatuses (e.g., light emitting diode (LED) backlights), organic light emitting diode (OLED) display apparatuses, plasma display apparatuses, CRT display apparatuses, and the like. The display apparatus 138 may display patient information, one or more medical images and/or videos, a graphical user interface, or a component received by the display apparatus 138 from the controller circuit 102, one or more 2D, 3D, or 4D ultrasonic image data sets from ultrasonic data stored in the memory 106, or an anatomical measurement, a diagnosis, processing information, and the like currently acquired in real time.

The user interface 142 controls the operation of the controller circuit 102 and the ultrasound imaging system 100. The user interface 142 is configured to receive an input from a clinician and/or an operator of the ultrasound imaging system 100. Optionally, the display apparatus 138 may be a touch screen display apparatus that includes at least a part of the user interface 142. For example, a part of the user interface 142 may correspond to a graphical user interface (GUI) that is generated by the controller circuit 102 and is shown on the display apparatus 138. The touch screen display apparatus may detect the presence of a touch from the operator on the display apparatus 138, and may also identify the location of the touch relative to the surface area of the display apparatus 138. For example, a user may select, by touching or contacting the display apparatus 138, one or more user interface components of the user interface (GUI) shown on the display apparatus. In addition, the user interface 142 may include a keyboard, a mouse, a trackball, a touch pad, one or more physical buttons, and the like. In some embodiments, the user interface 142 such as the keyboard, the mouse, the trackball, the touch pad, and the physical buttons described above is integrated on a control panel. The control panel may include a platform that facilitates an operation of a user. In a bench-top ultrasound imaging system, the platform-type control panel may be part of the overall ultrasound imaging system. In a portable ultrasound imaging system, the platform-type control panel may be part of a cart, and the cart may be used for placing and fixing the portable ultrasound imaging system.

With further reference to FIG. 1, the ultrasound imaging system 100 may include the probe 126. In the example of FIG. 1, the probe 126 is connected to the host 101 of the ultrasound imaging system 100 by means of the cable 110. However, it may be understood that in an optional instance, the probe may include a wireless probe, and accordingly, the probe only needs to be connected to the host 101 by means of wireless communication technology instead by means of the cable. The probe 126 may include elements (not shown) such as a transducer, a transmitter, a transmit beam former, and a detector/SAP electronics. The detector/SAP electronics may be used to control the switching of the transducer elements. The detector/SAP electronics may also be used to group the transducer elements into one or more sub-holes. Configurations of the probe 126 will also be described below exemplarily. The probe 126 may be any type of probe, including a linear probe, a curved array probe, a 1.25D array probe, a 1.5D array probe, a 1.75D array probe, or a 2D array probe. The probe 126 may alternatively be a probe used for volumetric imaging. For example, the probe 126 may be an electronic 4D (E4D) probe. In addition, the probe 126 may also be a mechanical probe, for example, a mechanical 4D probe or a hybrid probe. The probe 126 may be configured to acquire 4D ultrasound data, and the 4D ultrasound data includes information about how the volume changes over time, and may be processed to obtain a volumetric ultrasound image related to the site to be imaged. It can be understood that each volume may include a plurality of 2D images or slices, and accordingly, the controller circuit may select a required 2D image from the volumetric ultrasound images. In some other embodiments, the probe 126 may alternatively be a wireless probe. The wireless probe may use a built-in power supply to supply power to internal elements, so as to perform ultrasound scanning and/or data transmission. The wireless probe may also have a built-in wireless transmission module used to perform data transmission with the ultrasound imaging system 100.

Optionally, the controller circuit 102 may retrieve the digitized signals stored in the memory 106 for use in a beam former processor. For example, the controller circuit 102 may convert the digitized signal into a baseband signal or compress the digitized signal.

In some embodiments, the controller circuit 102 may further include a beam forming processor. The beam forming processor may include one or more processors. If desired, the beam forming processor may include a central processing unit (CPU), one or more microprocessors, or any other electronic component capable of processing the input data according to specific logic instructions. Additionally or alternatively, the beam forming processor may execute instructions stored on a tangible and non-transitory computer-readable medium (e.g., the memory 106) to perform beam forming computation using any suitable beam forming method, such as adaptive beam forming, synthetic emission focusing, aberration correction, synthetic aperture, clutter suppression, and/or adaptive noise control, etc.

In some embodiments, the controller circuit 102 may further include a radio frequency (RF) processor. The beam forming processor executes beam forming on the digitized signals of the transducer elements, and outputs an RF signal. The RF signal is then provided to the RF processor for processing the RF signal. The RF processor may include one or more processors. If desired, the RF processor may include a central processing unit (CPU), one or more microprocessors, or any other electronic component capable of processing the inputted data according to specific logic instructions. Additionally or alternatively, the RF processor may execute instructions stored on a tangible and non-transitory computer-readable medium (e.g., the memory 106). Optionally, the RF processor may be integrated with and/or be part of the controller circuit 102. For example, operations described as being executed by the RF processor may be configured to be executed by the controller circuit 102.

The RF processor may generate, for a plurality of scanning planes or different scanning modes, different ultrasonic image data types and/or modes, e.g., B-mode, color Doppler (e.g., color blood flow, velocity/power/variance), tissue Doppler (velocity), and Doppler energy, on the basis of a predetermined setting of a first model. For example, the RF processor may generate tissue Doppler data for multiple scanning planes. The RF processor acquires the information (e.g., I/Q, B-mode, color Doppler, tissue Doppler, and Doppler energy information) related to a plurality of data pieces, and stores the data information in the memory 106, where the data information may include time stamp and orientation/rotation information.

Optionally, the RF processor may include a composite demodulator (not shown) for demodulating the RF signal to generate an IQ data pair representing an echo signal. The RF or IQ signal data may be provided directly to the memory 106 so as to be stored (e.g., stored temporarily). If desired, an output of the beam forming processor may be delivered directly to the controller circuit 102.

The controller circuit 102 may be configured to process the acquired ultrasonic data (e.g., RF signal data or an IQ data pair), and prepare and/or generate an ultrasound image data frame representing an anatomical structure of interest so as to display the same on the display apparatus 138. The acquired ultrasonic data may be processed by the controller circuit 102 in real time when an echo signal is received in a scanning or treatment process of ultrasound examination. Additionally or alternatively, the ultrasonic data may be temporarily stored in the memory 106 in a scanning process, and processed in a less real-time manner in live or off-line operations.

The memory 106 may be used to store processed frames of acquired ultrasound data that are not scheduled to be immediately displayed, or may be used to store post-processed images (e.g., shear wave images and strain images), firmware or software corresponding to, for example, a graphical user interface, one or more default image display settings, programmed instructions, and the like. The memory 106 may store a medical image, such as a 3D ultrasound image data set of ultrasonic data, where such a 3D ultrasound image data set is accessed to present 2D and 3D images. For example, the 3D ultrasound image data set may be mapped to the corresponding memory 106 and one or more reference planes. Processing of ultrasound data that includes the ultrasound image data set may be based in part on user input, e.g., a user selection received at the user interface 142.

With further reference to FIG. 1, in some embodiments, the ultrasound imaging system 100 may further include the probe holder 120. The probe holder 120 may be used for placing an idle probe 126. In an actual scanning process, a user may select different types of probes 126 according to different anatomical structures of interest that need to be scanned. When not in use by the user, the probe 126 may be placed on the probe holder 120. The probe holder 120 may be an independent component separately placed in the vicinity of the ultrasound imaging system 100. In addition, the probe holder 120 may also be detachably connected to the ultrasound imaging system 100. The detachable probe holder 120 can be removed when not needed to further save space. In other embodiments, the probe holder 120 may be provided at an edge of a control panel of the ultrasound imaging system 100.

Different types of probes 126 typically have shapes and outer surface sizes due to different usage scenarios, different types of internal elements, and the like. For example, an intracavitary probe is typically configured to have an elongated structure to adapt to a lumen of the human body. Alternatively, a 4D probe is typically relatively large in size due to a transducer and other complex elements inside the 4D probe. However, some high-frequency superficial probes typically are small in size to adapt to various skin surfaces. In a practical application scenario, there are high stability requirements for holding of the probe. If a precision probe is dropped, it is very likely that an element will be damaged, affecting normal ultrasound scanning. Therefore, the probe holder needs to ensure a good fit with an outer surface of the probe to ensure a good holding effect. To that end, in some existing solutions, different types of probe holders are designed for different sizes of probes, and the user can fix different probes in corresponding holders, respectively. The process of matching a dedicated probe holder and a probe can distract the user.

Figure 2:
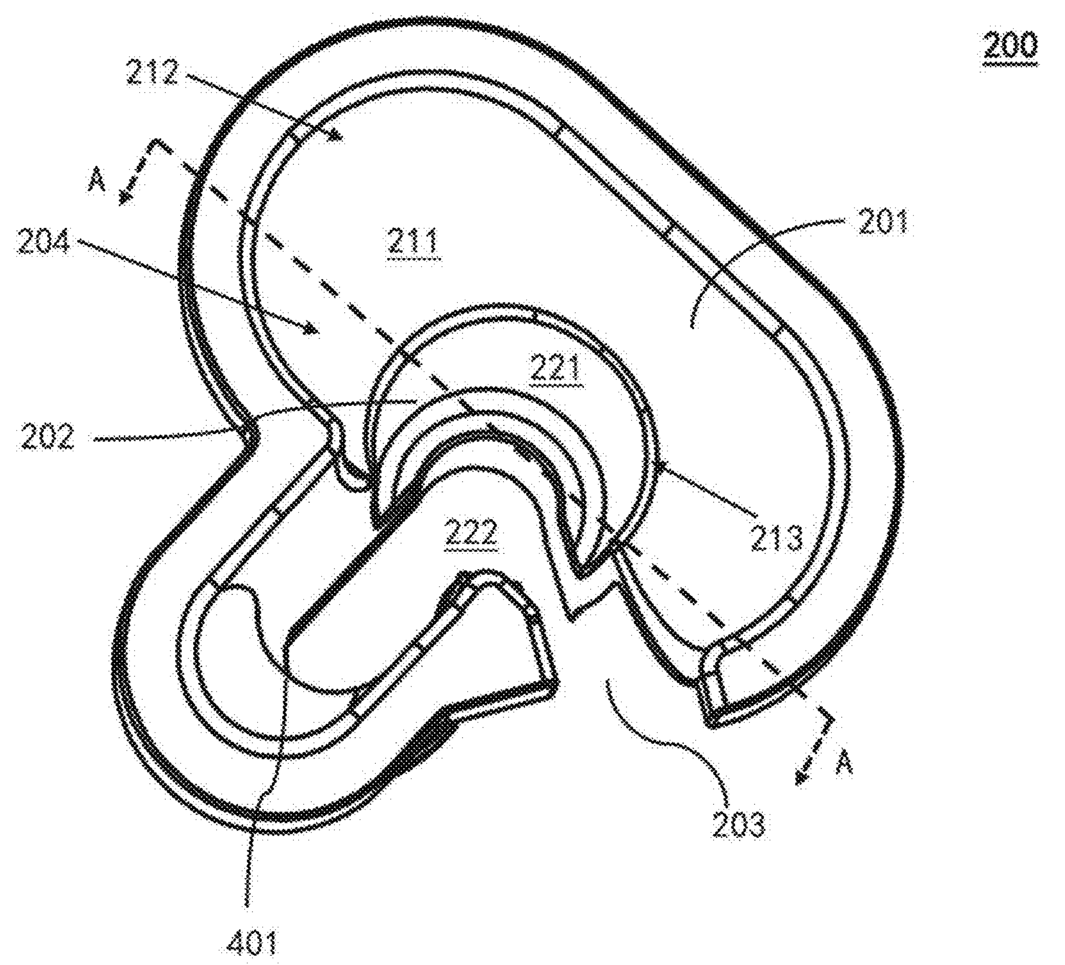
FIG. 2 is a perspective view of a probe holder 200 used for an ultrasound imaging system in some embodiments of the present application.

To solve at least the aforementioned problem, embodiments of the present application provide improvements. With reference to FIG. 2, FIG. 2 is a perspective view of a probe holder 200 used for an ultrasound imaging system in some embodiments of the present application. The probe holder 200 includes an upper holding portion 201, a lower holding portion 202, and a side opening 203.

The upper holding portion 201 includes a first cavity 211 formed by a surrounding inner surface 204. An upper end of the first cavity 211 includes an upper opening 212. The inner surface 204 contracts inward at a lower end of the first cavity 211 to form a lower opening 213. The size of the lower opening 213 is smaller than the size of the upper opening 212.

In addition, the lower holding portion 202 includes a second cavity 221 formed by the inner surface 204 passing through the lower opening 213 and continuing to extend downward a certain distance. The inner surface 204 contracts inward at a lower end of the second cavity 221 to form a bottom opening 222. The size of the bottom opening 222 is smaller than the size of the lower opening 213.

Furthermore, the side opening 203 penetrates outward through the probe holder 200 from the inner surface 204, and extends from the upper opening 212 to the bottom opening 222.

In the aforementioned configuration, one probe holder 200 simultaneously includes holding portions of different sizes. The first cavity 211 of the upper holding portion 201 is adapted to hold a large-sized probe, and the second cavity 221 of the lower holding portion 202 that is formed by means of the inner surface contracting and extending is adapted to hold a small-sized probe. Such an ultrasound probe holder exhibits better adaptability. When placing the probe, a user does not need to intentionally select a probe holder. For example, when the user needs to fix the probe, the user may first thread a cable to which the probe is connected through the side opening 203, and then place the probe. A large-sized probe can be in sufficient contact with an inner surface of the first cavity 211 and securely held. When a probe to be placed is small in size, the second cavity 221 formed by means of the inner surface 204 contracting downward and extending can come into sufficient contact with and support an outer surface of the small-sized probe. In this way, the same probe holder 200 adapts to probes of different outer surface sizes. In addition, the second cavity 221 is formed by means of the inner surface of the first cavity 211 extending downward. In this way, the inner surface 204 as a whole is a smooth and flat surface, and does not tend to cause a dead spot that is difficult to clean and disinfect, which also makes it easier for the user to perform disinfection and sterilization.

In some embodiments, the first cavity 211 is configured to hold a probe of a first size. The second cavity 221 is configured to hold a probe of a second size. The second size is smaller than the first size. It may be understood that the meanings of the first size and the second size mainly relate to the size of an outer surface of a bottom portion of the probe, because the probe holder is typically in contact with the aforementioned portion of the probe. In addition, the first size and the second size may deviate within a certain range that ensures that the probe holder and the surface of the probe are in sufficient contact with each other to facilitate holding of the probe. It should be noted that although some existing holders may have some enlarged openings on probe holding apparatuses to have the effect of guiding a probe, such a probe holder, as described above in the present application, is not capable of sufficiently holding the large-sized probe because the shape thereof is not specifically designed for a probe holding function. In the present application, regarding the shape of the inner surface of the first cavity 211 and the shape of an inner surface of the second cavity 221, contours of outer surfaces of different types of probes and stable holding of probes of at least two different sizes in a targeted manner are fully taken into account, while cleaning and disinfection dead spots caused by unevenness of the inner surfaces (for example, a step or a seam) are avoided.

Figure 3:
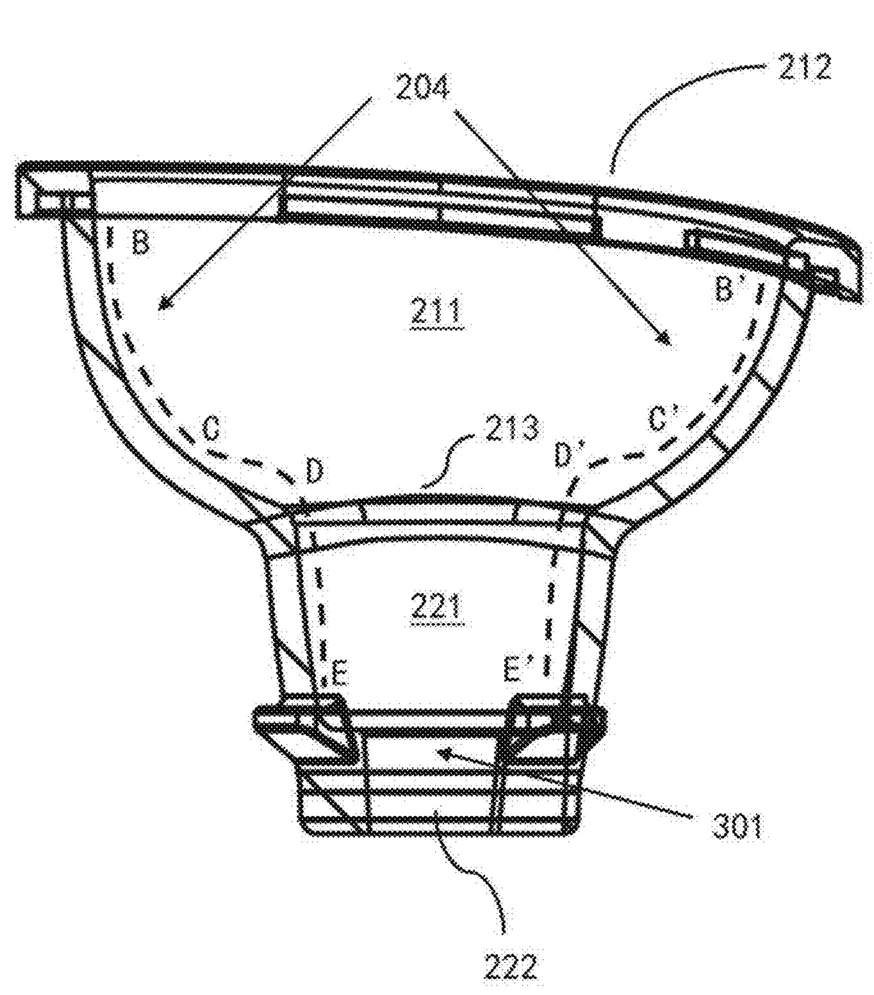
FIG. 3 is a cross-sectional view of the probe holder 200 of FIG. 2 along line A-A.

The probe holder of the present application is described in detail below with reference to FIG. 3. FIG. 3 is a cross-sectional view of the probe holder 200 of FIG. 2 along line A-A, to provide a more detailed and clear description of the internal structure of the probe holder 200.

As shown in FIG. 3, top-to-bottom contour lines B-C-D-E and B'-C'-D'-E' of the inner surface 204 of the probe holder 200 can be observed more clearly in the cross-sectional view along the line A-A. The first cavity 211 and the second cavity 221 each have a continuous and smooth inner surface. The first cavity 211 is used to hold the probe of the first size, the second cavity 221 is used to hold the probe of the second size, and the second size is smaller than the first size. The continuous and smooth inner surfaces are advantageous for fitting probes of a plurality of different sizes without causing a problem in which the probes are insecurely fixed due to not being able to achieve sufficient contact. For example, the first size may include a certain range of sizes, and the inner surface of the first cavity 211 is capable of adapting to large ultrasound probes of a plurality of different sizes. Similarly, the second size may also include a certain range, and the second cavity 221 is also applicable to a plurality of probes having small outer surface sizes. In addition, the continuous and smooth inner surfaces can further facilitate cleaning and disinfection of the probe holder. Because the probe acts as a component that is simultaneously in contact with a person to be scanned (for example, a patient) and the user (for example, a doctor), and the probe is often in contact with a reagent such as an acoustic couplant, the probe needs to be frequently cleaned and disinfected. The frequency and ease of cleaning and disinfection of the probe holder as a component in close contact with the probe are quite important. The continuous and smooth inner surfaces do not tend to cause dead spots, and therefore greatly help the user disinfect the probe holder.

In some embodiments, the inner surface 204 of the first cavity 211 includes a circular arc structure (segment B-C-D segment and segment B'-C'-D') that gradually contracts from the upper opening 212 to the lower opening 213. A part of the circular arc structure close to the lower opening 213 has a reduced curvature. For example, it can be seen from FIG. 3 that the curvature of segment C-D segment is less than the curvature of segment B-C segment. In such an arrangement, the inner surface 204 close to the lower opening 213 can be more flattened, thereby better fitting an outer surface of a large-sized probe.

In some other embodiments, the size of a part of the inner surface 204 of the first cavity 211 close to the upper opening 212 gradually increases to form a probe guide portion (a space surrounded by an inner surface between segment B-C segment and segment B'-C'). It can be seen from the cross-sectional view of FIG. 3 that the probe guide portion has a flared structure. Such a configuration enables the user to place the probe without needing to perform excessive alignment. Once the probe comes into contact with the inner surface of the first cavity 211, the probe guide portion of the flared shape can guide the probe to align with a suitable holding portion to achieve the effect of holding the probe.

Reference is further made to FIG. 3. In some embodiments, the inner surface 204 of the second cavity 221 contracts inward along a straight line (for example, segment D-E and segment D'-E' in FIG. 3) to form a cylindrical structure having a gradually decreasing inner diameter. Such a configuration can be more advantageous for holding a small-sized probe. On one hand, the cylindrical structure can better fit a small-sized probe, for example, a probe having a cylindrical end portion structure. On the other hand, the cylindrical structure having a gradually decreasing inner diameter enables the probe to be blocked after falling to a certain extent in the second cavity 221, so that the probe does not fall off easily and thus become damaged.

In some other embodiments, the bottom opening 222 further includes a stepped structure 301. The stepped structure 301 may be understood as being formed by the holder extending inward at the bottom opening 222 end. Such an arrangement can further reduce the size of the bottom opening 222. Even when a small-sized probe is to be placed, the probe can be securely fixed in the probe holder 200.

The inventors have further realized that in some usage scenarios, the probe may encounter a cable management problem after the probe is fixed on the probe holder. To be specific, after the probe is fixed on the probe holder, the probe is typically low to the ground, and a cable connecting the probe and a body of the ultrasound imaging system may hang down onto the ground. On the one hand, this can result in cable damage, and on the other hand, causes no change in moving the ultrasound imaging system. Therefore, in some embodiments, the inventors have further made improvements to the probe holder.

Figure 4:
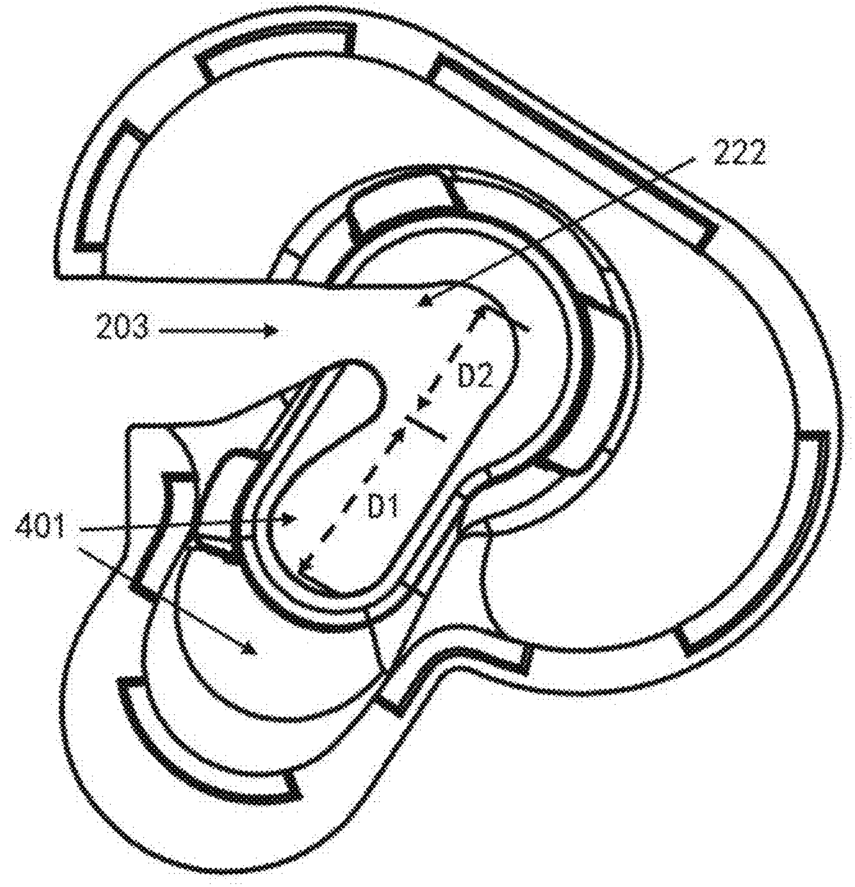
FIG. 4 is a bottom view of the probe holder 200 shown in FIG. 2.

Reference is made to FIG. 2 and FIG. 4. FIG. 4 is a bottom view of the probe holder 200 shown in FIG. 2.

In some embodiments, the probe holder 200 further includes a cable recess 401. The cable recess 401 is formed by the inner surface 204 extending outward from the bottom opening 222 to the upper opening 212. In addition, the cable recess 401 obliquely extends substantially along a straight line from the bottom opening 222 to the upper opening 212. In such a configuration manner, when the user is threading a cable of the probe through the side opening 203 into the empty cavity surrounded by the inner surface 204, the user can place the cable in the cable recess 401. In this case, a certain length of cable can be laid on the cable recess 401 once the user pulls the cable up. In addition, because the cable recess 401 is formed by outward extension and has a certain slope, the cable recess 401 can provide a certain friction force for the cable to prevent the cable from slipping off. Further, the design of extending obliquely along a straight line can prevent friction force from being excessively large and damaging the cable. Because the cable is laid on the cable recess 401, at that time the bottom opening 222 is not occupied by the cable. The user may thread again a cable near an end portion of the probe through the side opening 203 into the empty cavity surrounded by the inner surface 204, and in that case, the cable falls into the bottom opening 222. In other words, the user may loop the cable around the probe holder 200 to form a ring, to prevent the cable from dragging on the ground and can also still hold the probe within the probe holder 200.

To further improve a cable holding effect of the probe holder 200, some embodiments of the present application further provide improvements. With reference to FIG. 4, in some embodiments, the width of the cable recess 401 at the bottom opening 222 end gradually decreases from outside to inside. In other words, the width of the cable recess 401 is smallest at a position near the center of the bottom opening 222 and then extends outward while gradually increasing. In such a configuration, after the user places the cable of the probe in the cable recess, even if the user subsequently pulls the cable for adjustment, it can be ensured that the cable will not easily fall out of the cable recess.

Further, in some embodiments, an extension depth D1 of the cable recess 401 the bottom opening 222 end is greater than the diameter D2 of the bottom opening. Such a configuration can further ensure that the cable can be sufficiently accommodated in the cable recess 401 after entering the cable recess. On one hand, the cable does not easily escape even if the user drags the cable. On the other hand, when the user places the cable in the probe holder 200 again, the cable in the cable recess 401 does not spatially obstruct the cable penetrating the bottom opening 222.

It should be noted that the above shows various embodiments in which the inner surface of the probe holder 200 surrounds to form the cavity for holding of the probe and the cable recess for cable management, and the aforementioned embodiments may be reasonably combined with each other or selected under the teachings of the present disclosure. In addition, the outer surface of the probe holder 200 may have an arbitrary contour without affecting a probe holding function thereof. For example, the outer surface of the probe holder 200 may be a cup-shaped structure, a cylindrical structure, or a structure integrated with the ultrasound imaging system.

In addition, the probe holder 200 described in any one of the above-mentioned embodiments may further include an elastic body, the elastic body including the upper holding portion, the lower holding portion, and the side opening, the elastic body being detachably mounted in a body of the probe holder, and the size of an outer surface of the elastic body matching the size of an inner surface of the body of the probe holder. In other words, the structure related to the inner surface of the probe holder described in any one of the aforementioned embodiments may be formed by being surrounded by the elastic body. For example, components such as the upper holding portion, the lower holding portion, and the side opening of the probe holder 200 shown in FIG. 2 to FIG. 4 may be understood as being formed by being surrounded by an inner surface of the elastic body. Subsequently, the elastic body is then mounted in the body (not shown in the figures) of the probe holder. An exemplary description of a specific arrangement manner is provided below. The material of the elastic body may include any rubber or other polymer material in the art having resilient properties, or other materials having variable properties. This is not limited in the present application. In addition, the body of the probe holder may be understood as a housing of the elastic body. The inner surface of the body of the probe holder matches the elastic body to be configured to accommodate the above-mentioned elastic body, the outer surface of the body of the probe holder may be have various shapes, such as being cup-shaped or cuboid, and the body of the probe holder may be further attached to another component connected to the ultrasound imaging system. In other embodiments, the probe holder may include only the elastic body or only the body, and the specific configuration of the probe holder remains as described in any one of the embodiments of the present application and will not be repeated herein.

As described in the present application, the probe holder 200 may fit with the ultrasound imaging system in different manners. In some embodiments, the probe holder 200 may be a detachable independent component in the ultrasound imaging system, and the probe holder is fixed to the ultrasound imaging system in any detachable manner in the art, for example, insertion/removal, a threaded connection, engagement, etc. In some other embodiments, the probe holder 200 may be provided independently of the ultrasound imaging system. For example, the probe holder may be fixed at another position, such as a wall or a support, outside the ultrasound imaging system. In addition, the probe holder 200 may alternatively be part of the ultrasound imaging system, for example, provided on the control panel of the ultrasound imaging system. A manner in which the probe holder is provided on the control panel of the ultrasound imaging system is described in detail below.

Figure 5:
FIG. 5 is a schematic diagram of an ultrasound imaging system 500 including a probe holder 501 in some embodiments of the present application.
Figure 5:
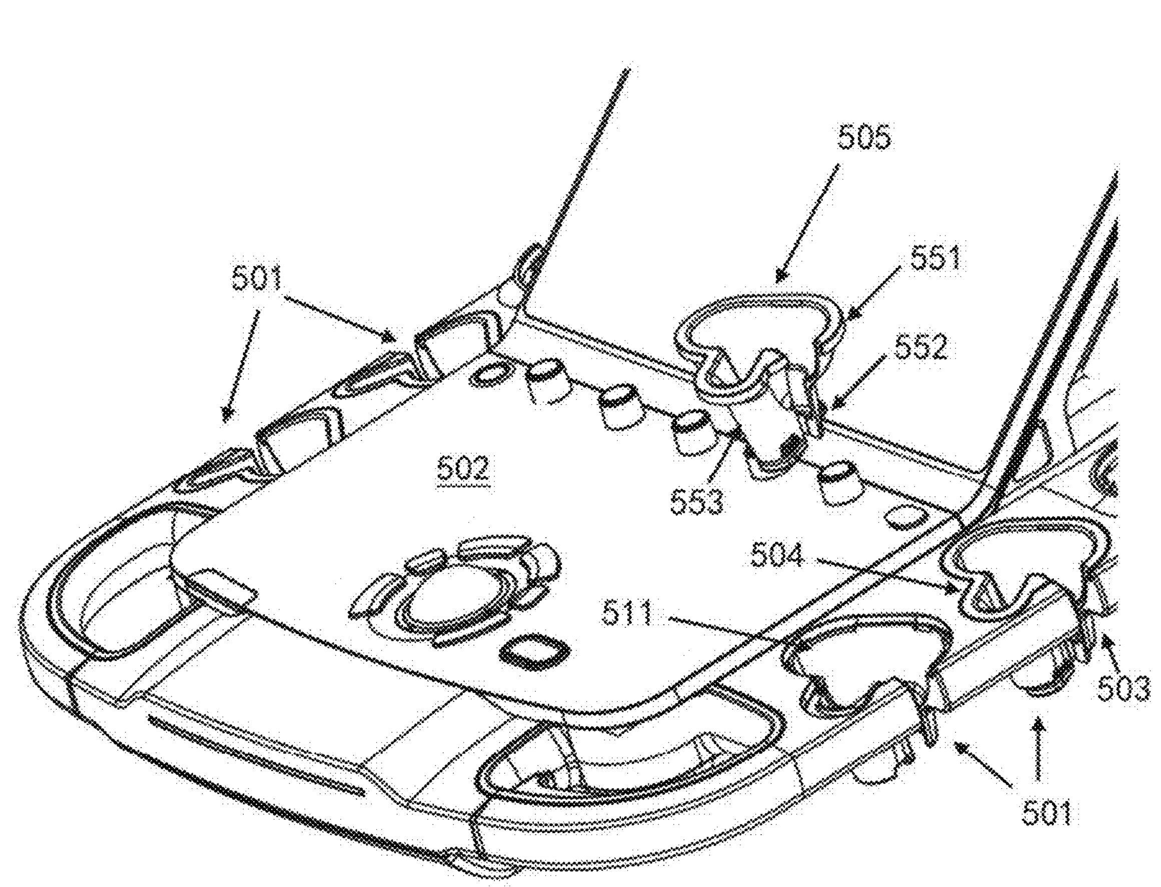

With reference to FIG. 5, FIG. 5 is a schematic diagram of an ultrasound imaging system 500 including a probe holder 501 in some embodiments of the present application. A configuration of the probe holder 501 is applicable to the description in any one of the aforementioned embodiments of the present application unless otherwise noted. It should be noted that FIG. 5 shows only a partial schematic diagram of the ultrasound imaging system 500 including the probe holder 501, and the configuration of other parts may be as described in any one of the aforementioned embodiments of the present application, or may be any configuration in the art.

As shown in FIG. 5, the probe holder 501 may be provided on a body of the ultrasound imaging system 500. For example, the probe holder may be provided at an edge of a control panel 502 of the ultrasound imaging system 500. This makes it easy for a user to access the probe in the probe holder 501, and does not hinder the user operating the control panel. In some examples, the ultrasound imaging system 500 is an integral bench-top ultrasound imaging system, and in this case, the control panel 502 is part of the entire ultrasound imaging system 500. In some other examples, the ultrasound imaging system 500 may be a portable ultrasound apparatus, and in this case, the control panel 502 may be a cart that supports the portable ultrasound apparatus. In some embodiments, the probe holder 501 may include a plurality of probe holders 501 provided at the edge of the control panel 502 of the ultrasound imaging system 500. The plurality of probe holders 501 have shapes that are the same as or symmetrical to each other. As shown in FIG. 5, the plurality of probe holders 501 may be provided on the same side or on opposite sides of the control panel 502. Probe holders 501 on the same side (for example, the left side or the right side) may have the same shape, and probe holders 501 on opposite sides may have symmetrical shapes. In other words, the universal probe holder 501 disclosed in the present application enables the design of the position of the probe holder on the control panel 502 to be simplified because the same type of probe holder 501 can be used to hold a plurality of different types of probes.

Further, in some embodiments, a side opening 503 and a cable recess 504 of the probe holder 501 may be disposed in a manner as shown in FIG. 5. The side opening 503 is configured to be disposed substantially perpendicularly to a side plate direction of the control panel 502, and there may be a certain included angle between the side opening 503 and a direction in which the cable recess 504 faces the front side (the side close to the user) of the control panel 502. In the described configuration, the side opening 503 is perpendicular to a side edge of the control panel 502, which can help the user quickly thread a cable of the probe through the side opening 503 for the next operation. Moreover, the means of design in which the cable recess 504 is biased toward the front side of the control panel 502 can ensure that it is more convenient and quick to drag the cable through the cable recess 504.

In some embodiments, the probe holder 501 may further include an elastic body 505. The elastic body 505 includes the upper holding portion, the lower holding portion, and the side opening. In other words, the elastic body provides the inner surface structure of the probe holder for holding the probe and/or managing the cable described in any one of the aforementioned embodiments. In addition, the elastic body 505 is detachably mounted in a body 511 of the probe holder 501. The size of an outer surface of the elastic body 505 matches the size of an inner surface of the body 511 of the probe holder 501. In such an arrangement, the elastic body 505 can more effectively fit an outer surface of the probe that needs to be held. For example, an arcuate inner contour of the upper holding portion of the elastic body 505 can be allowed to have a certain deviation from a contour of the probe that needs to be held. When the probe is placed on an inner surface of the upper holding portion, the elastic body 505 may be deformed to a certain extent to fit with the probe. Similarly, the diameter of a cylindrical inner contour of the lower holding portion of the elastic body 505 may not match the outer surface of the probe to a certain extent, and the cylindrical inner contour may be deformed to match the probe. In addition, the detachable elastic body 505 can also be easily mounted and dismounted for disinfection of the probe holder 501.

It should be noted that the aforementioned embodiment describes an illustration of the probe holder 501 that includes the elastic body 505 and that is provided on the ultrasound imaging system 500, but the arrangement manner including the elastic body is suitable for the probe holder described in any other embodiment of the present application.

In some embodiments of the present application, a connection means between the elastic body and the probe holder is optimized. With further reference to FIG. 5, in some embodiments, a top portion of the elastic body 505 includes a convex edge 551, a bottom portion of the elastic body 505 includes a plurality of protrusions 552, and the elastic body engages with an inner surface of the body 511 of the probe holder 501 by means of the convex edge 551 and the plurality of protrusions. The convex edge 551 may have the effect of limiting the elastic body 505 at an upper portion, and the protrusions 552 at a bottom portion can be deformed to pass through the body 511 (for example, pass through a second cavity of the body 511) of the probe holder 501, and can also return to an original shape after passing through the body, to implement quick engagement. Such a configuration manner enables the elastic body 505 to be quickly mounted and dismounted, and facilitates an operation of the user.

As described in the present application, the probe holder of the present application may further include the cable recess. In the embodiment in which the probe holder includes the elastic body, providing the cable recess can be more advantageous for quickly mounting and dismounting the elastic body. With further reference to FIG. 5, in some embodiments, the cable recess 553 of the elastic body 505 is formed by the inner surface extending outward from the bottom opening to the upper opening. Such a configuration manner has been described above, and will not be repeated herein. The shape of the cable recess 553 enables the elastic body 505 to be mounted in the body 511 of the probe holder 501 only from a certain specific angle. Specifically, because the shape of the cable recess 553 is formed by the elastic body 505 protruding outward, the shape is more advantageous for the user to align the elastic body 505 with the body 511 of the probe holder 501 than regular shapes such as an elliptical shape and a circular shape. In a specific usage scenario, the user only needs to roughly align the cable recess 553 on the elastic body 505 with a corresponding part on the body 511, and elastic body 505 can slide down to an accurate position without an offset. In contrast, regular shapes such as elliptical shapes and circular shapes are susceptible to angular rotation and are not easily aligned. The aforementioned embodiment of the present application enables the user to save more time when the user dismounts the elastic body 505 for disinfection and then replaces the elastic body.

A plurality of configuration manners of the probe holder have been described in the present application. In some embodiments, the probe holder has a first cavity of an arcuate structure having a continuous and intact inner surface and a second cavity having a continuous and intact inner surface, so that the same probe holder can adapt to a plurality of different probes. In some embodiments, the probe holder has the cable recess and therefore has both a probe holding function and a cable management function. In some embodiments, the designed cable recess not only facilitates placement of the probe cable, but also efficiently places the cable for escape. In some embodiments, providing an elastic body structure on an inner side of the probe holder can further improve the adaptability of the probe holder.

A plurality of configuration manners of the ultrasound imaging system including the aforementioned probe holder are also described in the present application. The ultrasound imaging system may be any system in the art, which can use the probe holder described in the present application. For example, the probe holder may be independent of and separated from the ultrasound imaging system. Alternatively, the probe holder may be detachably connected to the ultrasound imaging system in any quick dismounting manner. In addition, the probe holder may alternatively be integrated in the ultrasound imaging system as part of a body of the ultrasound imaging system.

The purpose of providing the above specific embodiments is to facilitate understanding of the content disclosed in the present invention more thoroughly and comprehensively, but the present invention is not limited to these specific embodiments. Those skilled in the art should understand that various modifications, equivalent replacements, and changes can also be made to the present invention and should be included in the scope of protection of the present invention as long as these changes do not depart from the spirit of the present invention.

The invention claimed is:

1. A probe holder for an ultrasound imaging system, comprising:

an upper holding portion, wherein the upper holding portion comprises a first cavity formed by a surrounding an inner surface, an upper end of the first cavity comprises an upper opening, the inner surface contracts inward at a lower end of the first cavity to form a lower opening, and the size of the lower opening is smaller than the size of the upper opening;

a lower holding portion, wherein the lower holding portion comprises a second cavity formed by the inner surface passing through the lower opening and continuing to extend downward by a certain distance, the inner surface contracts inward at a lower end of the second cavity to form a bottom opening, and the size of the bottom opening is smaller than the size of the lower opening; and a side opening, wherein the side opening penetrates outward through the probe holder from the inner surface, and extends from the upper opening to the bottom opening, wherein the inner surface of the upper holding portion tapers inward at a curvature, and the inner surface of the lower holding portion tapers inward along a straight line, further comprising an elastic body, wherein the elastic body comprises an upper holding portion, a lower holding portion, and a side opening, the elastic body is detachably mounted in a body of the probe holder, and a size of an outer surface of the elastic body matches a size of the inner surface of upper holding portion and the inner surface of the lower holding portion, wherein the elastic body further comprises a cable recess, wherein the cable recess is formed by the inner surface of the elastic body extending outward from the bottom opening to the upper opening, and the shape of the cable recess enables the elastic body to be mounted in the body of the probe holder.

2. The probe holder according to claim 1, wherein:

the first cavity and the second cavity each have a continuous and smooth inner surface, the first cavity is configured to hold a probe of a first size, the second cavity is configured to hold a probe of a second size, and the second size is smaller than the first size.

3. The probe holder according to claim 1, wherein:

an inner surface of the first cavity comprises a circular arc structure that gradually contracts from the upper opening to the lower opening, and a part of the circular arc structure close to the lower opening has a reduced curvature.

4. The probe holder according to claim 3, wherein:

the size of a part of the inner surface of the first cavity close to the upper opening gradually increases to form a probe guide portion.

5. The probe holder according to claim 1, wherein:

an inner surface of the second cavity contracts inward along a straight line to form a cylindrical structure having a gradually decreasing inner diameter.

6. The probe holder according to claim 1, wherein:

the bottom opening comprises a stepped structure.

7. The probe holder according to claim 1, further comprising:

a cable recess, wherein the cable recess is formed by the inner surface extending outward from the bottom opening to the upper opening, and the cable recess obliquely extends along a straight line from the bottom opening to the upper opening.

8. The probe holder according to claim 7, wherein:

an extension depth of the cable recess at the bottom opening end is greater than the diameter of the bottom opening.

9. The probe holder according to claim 1, wherein:

a top portion of the elastic body comprises a convex edge, a bottom portion of the elastic body comprises a plurality of protrusions, and the elastic body engages with the inner surface of the upper holding portion and the inner surface of the lower holding portion by means of the convex edge and the plurality of protrusions.

* * * * *